(12) United States Patent
Gaylord

(10) Patent No.: US 7,264,605 B2
(45) Date of Patent: *Sep. 4, 2007

(54) KNEE SUPPORT DEVICE FOR APPLYING RADIAL PRESSURE

(75) Inventor: Eric Lee Gaylord, Wadesboro, NC (US)

(73) Assignee: Medical Specialties, Inc., Charlotte, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 10/956,417

(22) Filed: Oct. 1, 2004

(65) Prior Publication Data

US 2005/0070832 A1    Mar. 31, 2005

Related U.S. Application Data

(63) Continuation-in-part of application No. 10/112,813, filed on Mar. 29, 2002, now Pat. No. 6,852,088.

(51) Int. Cl.
*A61F 5/00* (2006.01)
(52) U.S. Cl. .............................. 602/26; 602/62; 602/75
(58) Field of Classification Search ............ 602/26, 602/5, 6, 19, 23, 60–63, 75; 2/22, 24, 911; 128/882, 892, 881; 165/104.33, 104.21, 165/104.4; 361/700; 257/714, 715; 428/224, 428/230, 231, 252, 253, 258, 259
See application file for complete search history.

(56) References Cited

U.S. PATENT DOCUMENTS

| | | | |
|---|---|---|---|
| 4,334,528 A | 6/1982 | Gauvry | |
| 4,353,362 A | 10/1982 | DeMarco | |
| 4,777,946 A | 10/1988 | Watanabe et al. | |
| 4,836,194 A | 6/1989 | Sebastian et al. | |
| D307,054 S | 4/1990 | Johnson, Jr. | |
| 5,024,216 A * | 6/1991 | Shiono ........................ | 602/26 |
| 5,038,760 A | 8/1991 | Osborn | |
| 5,086,759 A | 2/1992 | Buddingh | |
| 5,147,261 A | 9/1992 | Smith et al. | |
| 5,399,150 A | 3/1995 | Saunders | |
| 5,417,646 A | 5/1995 | Gauvry | |
| 5,551,085 A | 9/1996 | Leighton | |

(Continued)

OTHER PUBLICATIONS

Marketing material from Aircast Devices website—Printed Apr. 2, 2003 (1 page).

(Continued)

*Primary Examiner*—Justine R. Yu
*Assistant Examiner*—Shumaya Ali
(74) *Attorney, Agent, or Firm*—Summa, Allan & Additon, P.A.

(57) ABSTRACT

An adjustable support device for the knee provides in one embodiment a strap, a primary tensioning device positioned on the strap, and a secondary tensioning device carried on the strap. A preferred embodiment of the device includes an elongate bar secured to the strap between first and second ends of the strap by a patch of material, stitching, or any number of known adhesives. The secondary tensioning device may include one or more patches of elastic, or alternatively, inelastic material that provide radially-directed pressure against the knee joint. In another embodiment, the secondary tensioning device provides pairs of ligatures secured to each end of the elongate bar for concentrating radially-directed pressure against the knee joint.

61 Claims, 9 Drawing Sheets

U.S. PATENT DOCUMENTS

| | | |
|---|---|---|
| 5,556,374 A | 9/1996 | Grace et al. |
| 5,560,046 A | 10/1996 | Iwamasa et al. |
| 5,586,969 A | 12/1996 | Yewer, Jr. |
| 5,591,122 A | 1/1997 | Yewer, Jr. |
| 5,656,023 A | 8/1997 | Caprio, Jr. et al. |
| 5,693,006 A | 12/1997 | Slautterback |
| 5,865,777 A | 2/1999 | Detty |
| 5,984,885 A | 11/1999 | Gavlord, Jr. et al. |
| 6,066,108 A | 5/2000 | Lundberg |
| 6,080,124 A | 6/2000 | Falk et al. |
| 6,099,490 A * | 8/2000 | Turtzo .................. 602/19 |
| 6,336,908 B1 | 1/2002 | Slautterback |
| 6,342,044 B1 | 1/2002 | Frangi et al. |
| 6,402,712 B1 | 6/2002 | Gauvry |
| 6,419,652 B1 | 7/2002 | Slautterback |
| 6,485,448 B2 | 11/2002 | Lamping et al. |
| 7,001,348 B2 * | 2/2006 | Garth et al. .................. 602/5 |

OTHER PUBLICATIONS

Marketing material from Pro-Tec Knee Support website—Printed Apr. 2, 2003 (1 page).

Marketing material from Pro Brand Sports Industries, Inc. website—Printed Apr. 2, 2003 (4 pages).

Marketing material from Brace International website—Printed Apr. 2, 2003 (1 page).

Marketing material from Cho-Pat Sport Medical Devices website—Printed Apr. 2, 2003 (1 page).

* cited by examiner

KNEE SUPPORT DEVICE FOR APPLYING RADIAL PRESSURE

CROSS-REFERENCE TO RELATED APPLICATIONS

This is a continuation-in-part application claiming benefit of copending U.S. application Ser. No. 10/112,813, filed Mar. 29, 2002 now U.S. Pat. No. 6,852,088, for Adjustable Support Device for the Knee. The copending application is commonly assigned with this application and is hereby incorporated entirely herein by reference.

BACKGROUND OF THE INVENTION

This invention relates to an adjustable support device for use in alleviating pain associated with a variety of conditions affecting the knee. Although the support device of the present invention is specifically intended for use by athletes to correct deficiencies in patellar tracking and to treat patellar tendonitis, the support device is equally suited for use in treating individuals who suffer from a variety of conditions affecting the knee and who require supplemental support to relieve pain and/or preserve the mobility of the knee joint. The support device is thus suitable for alleviating the symptoms of several conditions including, but not limited to, injuries to the anterior and posterior cruciate ligaments, the medial and lateral collateral ligaments, and injuries that cause the various muscular etiologies of patellofemoral pain syndrome.

While prior art straps and other devices exist which attempt to alleviate pain associated with the knee, knee joint and related tissues, such devices seldom apply a sufficient amount of pressure to the affected area to adequately relieve the discomfort suffered by the wearer. To the extent such devices do manage to apply any pressure to the knee, such pressure is usually distributed equally across the device and is thus inefficiently and incorrectly applied to the knee. Furthermore, the manner in which the ends of prior art devices extend around the knee, overlap each other and are connected together compromises the maximum amount of pressure the device is actually capable of achieving and applying to the knee. This is because a small amount of the tension achieved in the device when the device is stretched around the knee is inevitably lost when the wearer loosens his or her grip on one end of the device so that the other end can be connected thereto.

The present invention overcomes the inadequacies of prior art devices by providing an adjustable support device which utilizes elastomeric materials to apply pressure to specific aspects of an injured knee. The device is adjusted using two separate mechanisms to create two levels of tension to be applied to the knee, without sacrificing the total amount of tension created when the ends of the device are wrapped around the knee and connected together. The support device has a narrow end that fits through a slit that extends through the other, wider end of the device. Once the narrow end passes through the slit, the wearer adjusts the first level of tension by grasping and pulling on each end of the device and then attaching the ends directly to the outer surface of the device using male hook fastener patches which cling to the outer surface of the device. The second level of tension is then adjusted using a supplemental or secondary tensioning device that permits the wearer to apply a concentrated amount of radially-directed pressure to a specific area of the knee to relieve specific symptoms associated with that area.

OBJECT AND SUMMARY OF THE INVENTION

Therefore, it is an object of the present invention to provide an adjustable support device for relieving the symptoms associated with patella tendinitis and other conditions affecting the knee.

It is another object of the present invention to provide an adjustable support device that may be adjusted without loosening or removing the device from around the knee to alter the amount of compression applied by the device to the knee.

It is another object of the present invention to provide an adjustable support device that is easy to position around the right or left knee, or around the leg adjacent thereto.

It is another object of the present invention to provide an adjustable support device that can be quickly placed around and removed from the knee without difficultly and without requiring specialized medical training.

It is another object of the present invention to provide an adjustable support device that encircles the knee and provides a consistent level of radially-directed compression around the circumference of the knee while providing an enhanced, concentrated level of compression to a preselected portion of the anatomy of the knee.

These and other objects of the invention are achieved in the preferred embodiments disclosed below by providing an adjustable support device for the knee. The device includes an elongate strap having at least one elastic portion, and first and second ends for being secured around the knee in a tensioned condition and providing supplemental support to the patella, knee joint, and attachment sites of the connective tissues of the knee joint. A primary tensioning device is positioned on the strap for securing the device around the lower leg and positioning the strap in a primary tensioned position relative to the patella, knee joint, and attachment sites of the connective tissues of the knee joint. Another tensioning device or secondary tensioning device is carried by the strap and includes an elastic element and at least one attachment member for being placed in a secondary tensioned position relative to the strap for increasing the tension of the device and applying concentrated radially-directed pressure to the knee joint, attachment sites of the connective tissues of the knee joint, to the knee joint, attachment sites of the connective tissues of the knee joint, and an anterior aspect of the patella. In an alternative embodiment, the secondary tensioning device includes an inelastic element and at least one attachment member.

According to one preferred embodiment of the invention, the primary tensioning device includes first and second fasteners attached to the first and second ends, respectively, and cooperating with an outer surface of the strap for securing the strap around the lower leg and placing the strap in the primary tensioned position. The first and second fasteners are each preferably a patch of hooked material complementary to the outer surface of the strap.

According to another preferred embodiment of the invention, the outer surface is formed from looped material complementary to the first and second fasteners.

In another preferred embodiment of the invention, the primary tensioning device includes an opening defined by and extending through the strap adjacent the first end. The opening is adapted for receiving the second end of the strap therethrough, thereby permitting the tension on the strap to be increased prior to placing the strap in the primary tension position and without removing the strap from around the knee.

Yet another preferred embodiment of the invention provides a primary tensioning device that includes an opening defined by and extending through the strap adjacent the second end. The opening is adapted for receiving the first end therethrough, thereby permitting tension on the strap to be increased prior to placing the strap in the primary tension position and without removing the strap from around the knee.

Still another preferred embodiment of the invention provides an opening that is an elongate slot extending perpendicularly to the longitudinal axis of the strap for permitting ease of movement of the end of the strap therethrough.

According to yet another preferred embodiment of the invention, a protective patch covers a side edge defining the opening for preventing wear to the side edge resulting from repeated placement of the end of the strap through the opening.

In still another preferred embodiment of the invention, the strap includes a centrally-disposed portion positioned between and integrally formed with the first and second ends for being placed over the knee joint, attachment sites of the connective tissues of the knee joint, and the anterior aspect of the patella.

According to another preferred embodiment of the invention, the centrally-disposed portion is defined by opposing, arcuate side edges of the strap for providing a supporting fit against the convex shape of the patella.

In yet another preferred embodiment of the invention, the centrally-disposed portion includes a width greater than the width of each of the first and second ends for permitting pressure to be applied by the centrally-disposed portion to an increased surface area of the knee.

Still another preferred embodiment of the invention, the longitudinal axis of the secondary tensioning device is aligned with the longitudinal axis of the strap, thereby increasing the amount of concentrated, radially-directed support pressure applied to the knee joint, connective tissues of the knee joint, and anterior aspect of the patella.

Yet another preferred embodiment of the invention, the strap includes interior walls defining a chamber for receiving the elastic element of the secondary tensioning device therein.

According to yet another preferred embodiment of the invention, the elastic element includes one or more patches of material.

In another preferred embodiment of the invention, the secondary tensioning device includes two attachment members connected to respective opposing side edges of the elastic element and releasably connected to the outer surface of the strap for placing the secondary tensioning device in the secondary tensioned position.

In yet another preferred embodiment of the invention, each of the attachment members is a patch of hooked material complementary to the outer surface of the strap.

According to another preferred embodiment of the invention, the elastic element is positioned within the chamber and is axially movable independent of the strap or primary tensioning device between a contracted position in the absence of tension on the elastic element and an expanded position in response to laterally-directed forces on the respective opposing side edges of the elastic element, thereby permitting the secondary tensioning device to be placed in the secondary tension position relative to the strap.

In another preferred embodiment of the invention, the secondary tensioning device includes first and second pairs of ligatures interconnecting the attachment element with the elastic element for preventing loss of the attachment element when not in use.

According to yet another preferred embodiment of the invention, the first and second pairs of ligatures extend through respective pairs of openings defined in the strap, thereby permitting the elastic element to be positioned within the chamber while simultaneously permitting the attachment member to be releasably attached to the outer surface of the strap.

In yet another preferred embodiment of the invention, a semi-rigid, elongate bar is positioned within the chamber between the elastic element and the interior wall adjacent to the wearer's knee. The bar may be secured to the strap by any number of known adhesives. The bar cooperates with the elastic element for directing the concentrated, radially-directed support pressure to the knee joint, attachment sites of the connective tissues of the knee joint, and the predetermined aspect of the patella.

According to yet another preferred embodiment of the invention, an adjustable support device for supporting a wearer's knee is provided that includes an elongate strap with at least one elastic portion, and first and second ends for being secured around the knee in a tensioned condition and providing supplemental support to the patella, knee joint, and attachment sites of the connective tissues of the knee joint. A primary tensioning device is positioned on the strap for securing the strap around the lower leg and positioning the strap in a primary tensioned position relative to the patella, knee joint, and attachment sites of the connective tissues of the knee joint. A secondary tensioning device is also included, and has at least one attachment member carried on the outer surface of the strap and connected to an elastic element positioned within a chamber defined by interior walls of the strap. The secondary tensioning device is adapted for being placed in a secondary tensioned position relative to the strap for increasing the tension of the strap and applying concentrated radially-directed support pressure to a knee joint, the attachment sites of the connective tissues of the knee joint, and an anterior aspect of the patella.

BRIEF DESCRIPTION OF THE DRAWINGS

FIG. 6B FIG. 6 is a cross-sectional view of another embodiment of the support device taken along line 6-6 of FIG. 1.

DETAILED DESCRIPTION OF THE INVENTION

Figure 1:
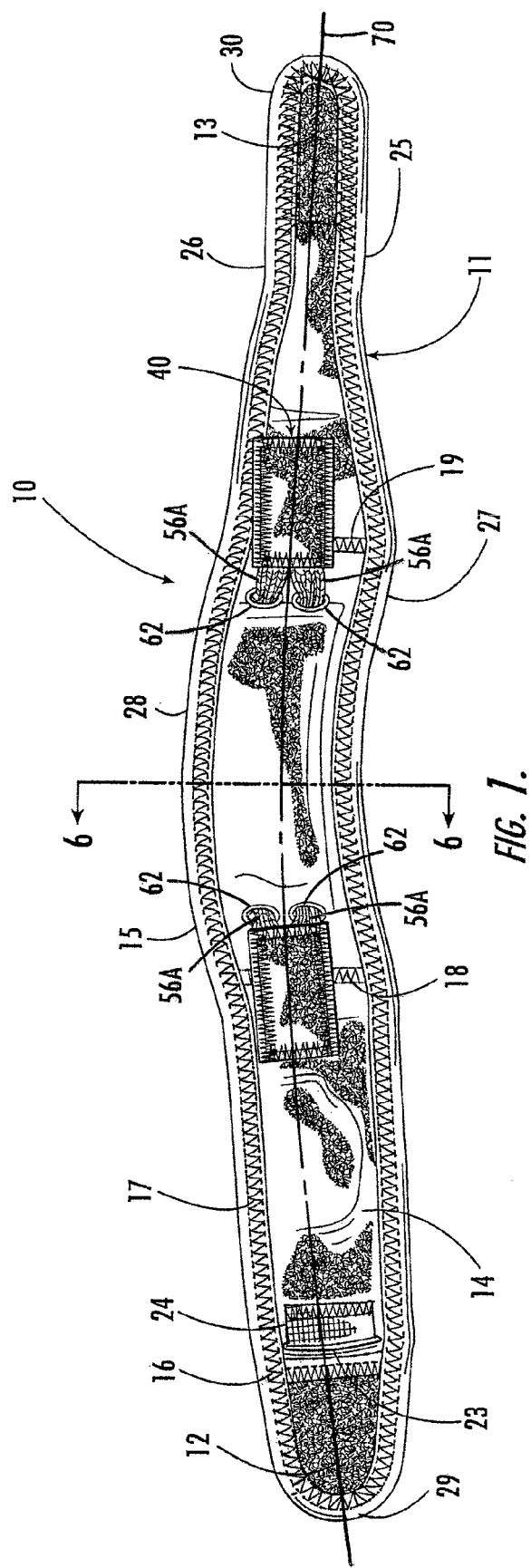
FIG. 1 is a front elevation of an adjustable support device according to one embodiment of the invention.
Figure 2:
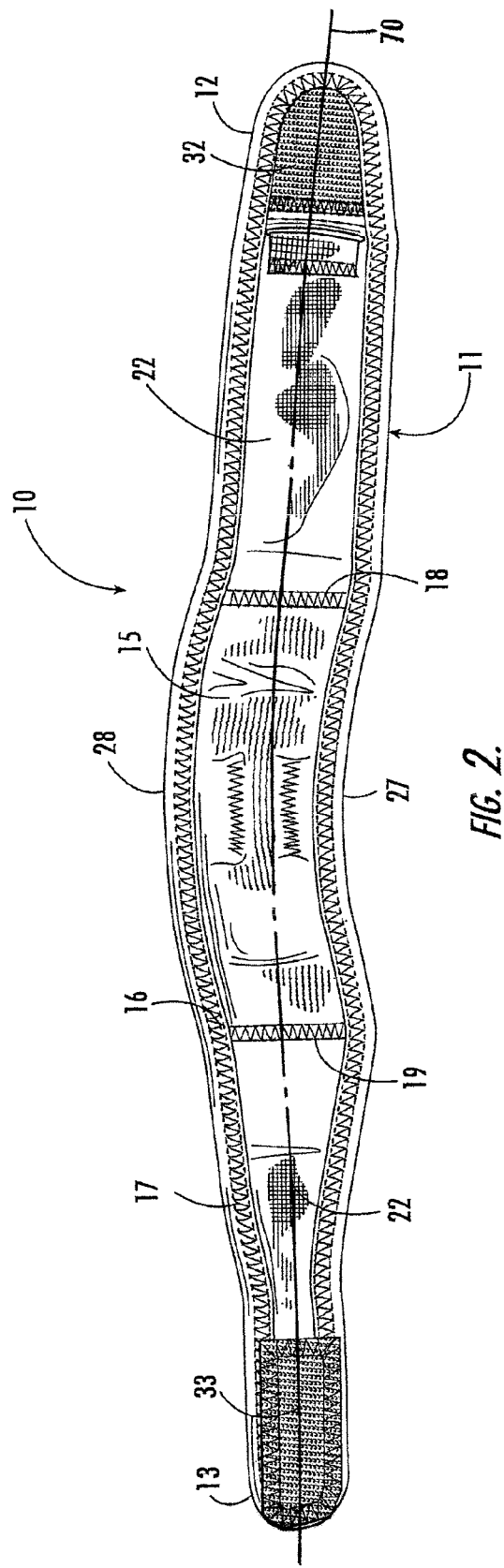
FIG. 2 is a rear elevation of the support device according to FIG. 1.

Referring now generally to the drawings, an adjustable support device is illustrated in FIG. 1 and shown generally at reference numeral 10. The support device 10 includes an elongate strap 11 that has first and second ends 12 and 13, respectively. As illustrated in FIG. 2, the strap 11 is formed from a front panel 14 and a back panel 15 which are overlaid with each other. The peripheral edge of panel 14 and one of the pairs of opposing side edges of back panel 15 are joined together and covered by a narrow strip of binding 16. The strip of binding 16 is preferably attached to the strap 11 using a row of zig-zag stitches 17 that extends around the perimeter of the front panel 14 adjacent the peripheral edge. Additional seams 18 and 19 formed by respective rows of zig-zag stitches extend across the width of the strap 11 and the back panel 15 to the front panel 14.

Although the front panel 14 may be formed from any suitable material, the front panel 14 is preferably formed from a neoprene replacement material having a raised, fibrous outer surface 20, a foam core 21 (see FIG. 6), and a smooth backing material 22 (see FIG. 2). Referring again to FIG. 1, a narrow slit 23 extends through the strap 11 adjacent end 12. Second end 13 is placed through slit 23 when the device 10 is secured in place around the knee of the wearer. A reinforcing patch 24 of knitted material covers and protects one of the edges defining the slit 23, to prevent end 13 from causing excessive wear to the slit 23, during use.

As is shown in FIG. 1, the strap 11 is specifically contoured to fit the anatomy of the knee. In particular, the elongate shape of the strap 11 is defined by opposing side edges 25 and 26 each of which extends along the longitudinal axis of the strap 11. Side edges 25 and 26 have inwardly and outwardly curved portions 27 and 28, respectively, that complement the convexity of the patella when the support 10 is being worn. Side edges 25 and 26 extend between and interconnect rounded edges 29 and 30 to define ends 12 and 13, respectively. While each of the ends 12 and 13 has a tapered shape, the width of end 13 is narrower than the width of end 12, which permits end 13 to fit through the slit 21 when the support 10 is worn.

Referring now to FIG. 2, the back of the support 10 is shown. The back panel 15 is positioned between the curved portions 27 and 28, and is attached to the front panel 14 using stitches 17 and seams 18 and 19. Although the back panel 15 may be formed from any suitable substance, the back panel 15 is preferably formed from a neoprene replacement material identical to that used to form the front panel 14, and thus has an outer surface having features identical to those of outer surface 20.

As is shown in FIG. 2, patches 32 and 33 of male hook fasteners are attached to the back surface 22 of front panel 14 adjacent ends 12 and 13, respectively. Patches 32 and 33 are not only used to connect ends 12 and 13 together to hold the strap 11 in place around the wearer's knee, but are also used in cooperation with the elastic qualities of the fabric materials used to form the front and back panels 14 and 15, respectively, to vary the degree of radially-directed pressure placed by the strap 11 around the circumference of the knee. While the male hook fastener patches 32 and 33 are preferably used to attach the back surface 22 to the outer surface 20 of front panel 14, complementary snaps, hook-and-eye fasteners, or any other type of suitable fastening devices may alternatively be used.

Figure 3:
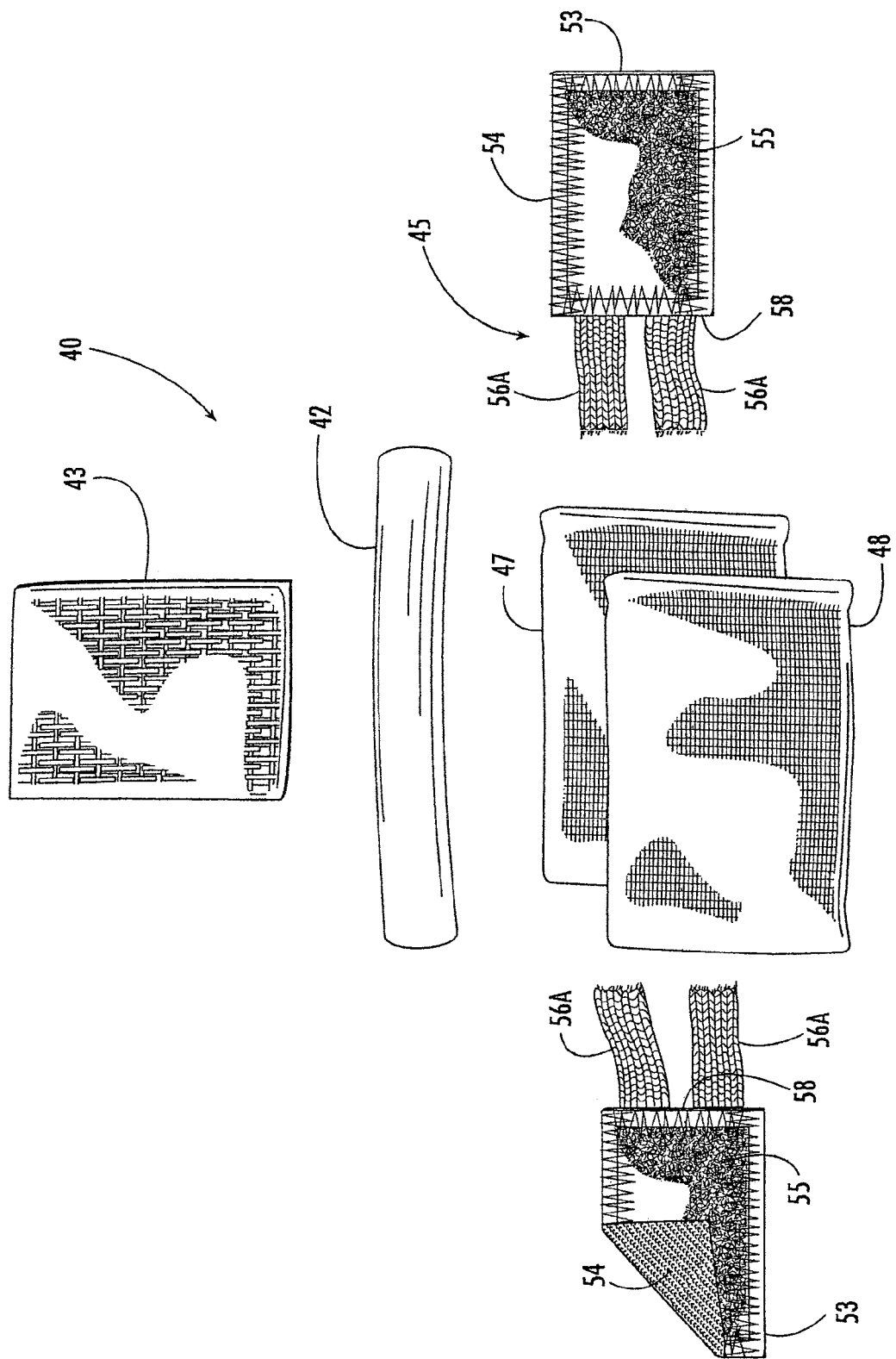
FIG. 3 is an exploded perspective view of components of the secondary tensioning device included in the support device prior to assembly.

Referring again to FIG. 1, the device 10 also includes a supplemental or secondary tensioning device 40 that permits the wearer to control the extent to which a concentrated amount of additional, radially-directed pressure is applied to a specific part of the knee. The components of the tensioning device 40 are shown in FIG. 3. The device 40 includes a short rod or bar 42 formed from a semi-rigid material, and a small patch 43 of knitted material. While the rod 42 is preferably a three-inch length of neoprene or nylon-braided cord having a ⅜ inch diameter, the bar 42 may alternatively have any suitable dimensions formed from any suitable material, and have any cross-sectional shape. For example, the bar 42 may also be formed from rubber material. Specifically, the rod or bar 42 must be sufficiently pliable to conform to the surfaces of the wearer's knee, yet sufficiently stable so as not to compress flat against the knee.

Figure 5:
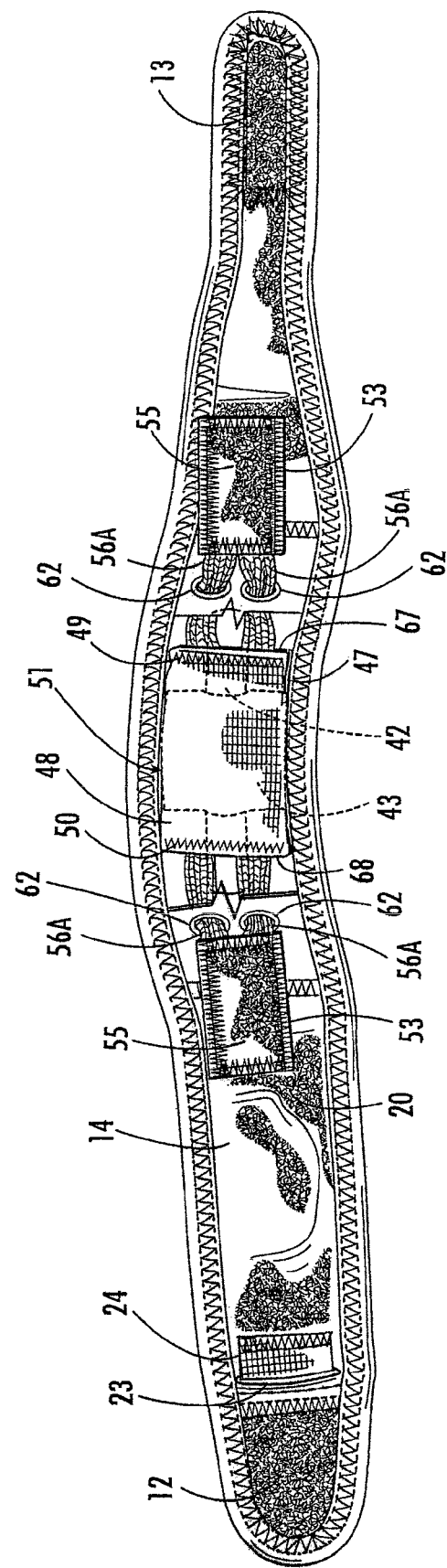
FIG. 5 is a partial cutaway view of the support device illustrating the manner in which the components of the secondary tensioning assembly are positioned relative to the support device.

The device 40 also includes a pliable pressure applicator 45, which is capable of being stretched along its length and used to apply a radially-directed force on the rod 42, which in turn causes the rod 42 to be compressed against a predetermined area of the knee. As illustrated in FIG. 5, the applicator 45 may include two patches of elastic or elastomeric material 47 and 48 which are overlaid in registration with one another and sewn together along opposing side edges using seams of zig-zag stitches 49 and 50 to form a central patch 51. Each patch 47 and 48 is preferably formed from a strip of elastic having a length of between 1.25 and 1.5 inches. Alternatively, the applicator 45 may include a single patch 48 of elastic or elastomeric material that forms the central patch 51. As used herein, the term "elastomeric" refers to any various elastic substances resembling rubber. It will be understood by those of skill in the art that the single patch 48 or double patches 47 and 48 forming the central patch 51 may also be formed from inelastic material such as nylon webbing or other known inelastic material of suitable strength.

Referring again to FIG. 3, the applicator 45 also includes two fastener patches 53. Each patch 53 is preferably formed from the same material as front and back panels 14 and 15, and has an inner surface 54 covered with male hook fasteners and an outer surface 55 having a raised, fibrous texture. Two string segments 56A are connected to a side edge 58 of each patch 53. Each segment 56A may be formed from any type of string or elongate material. In a preferred embodiment, each segment 56A is preferably formed from a short length of a conventional shoelace. As described below with reference to FIG. 5, each pair of segments 56A interconnects one of the fastener patches 53 with the central patch 51.

Figure 4:
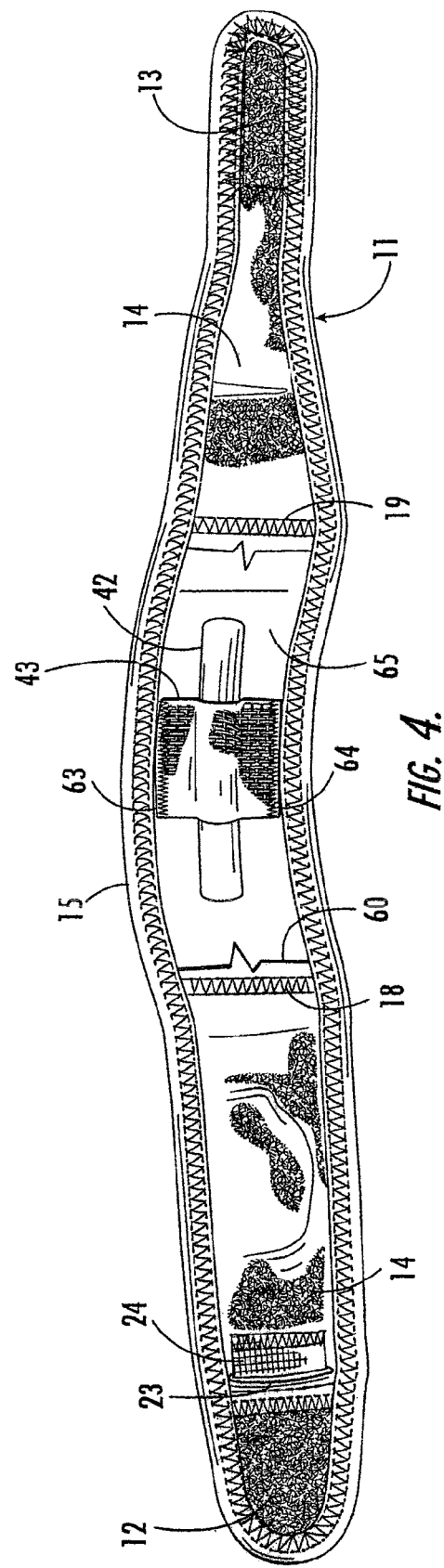
FIG. 4 is a partial cutaway view of the support device according to FIG. 2 wherein part of the secondary tensioning assembly is removed.
Figure 6:
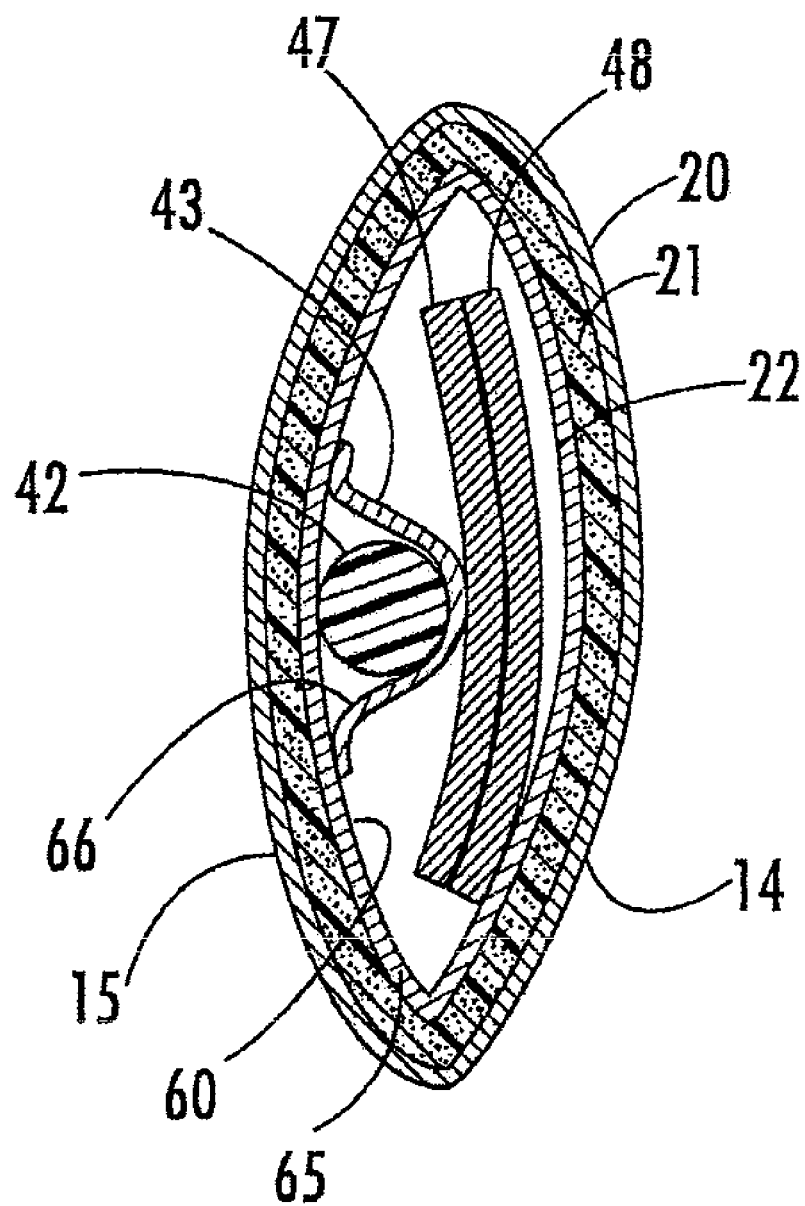
FIG. 6 is a cross-sectional view of one embodiment of the support device taken along line 6-6 of FIG. 1.

Referring now to FIGS. 4 and 5, the manner in which the components of the secondary tensioning device 40 are assembled and connected to the strap 11 is shown. As is shown in FIG. 4, the front and back panels 14 and 15 and seams 18 and 19 define an interior compartment or chamber 60 within which the rod 42 and patch 43 are positioned. As depicted in FIG. 6, opposing side edges 63 and 64 of the patch 43 are attached to the inside surface 65 of the back panel 15 that the patch 43 forms a loop 66 through which the rod 42 is positioned.

Figure 5A:
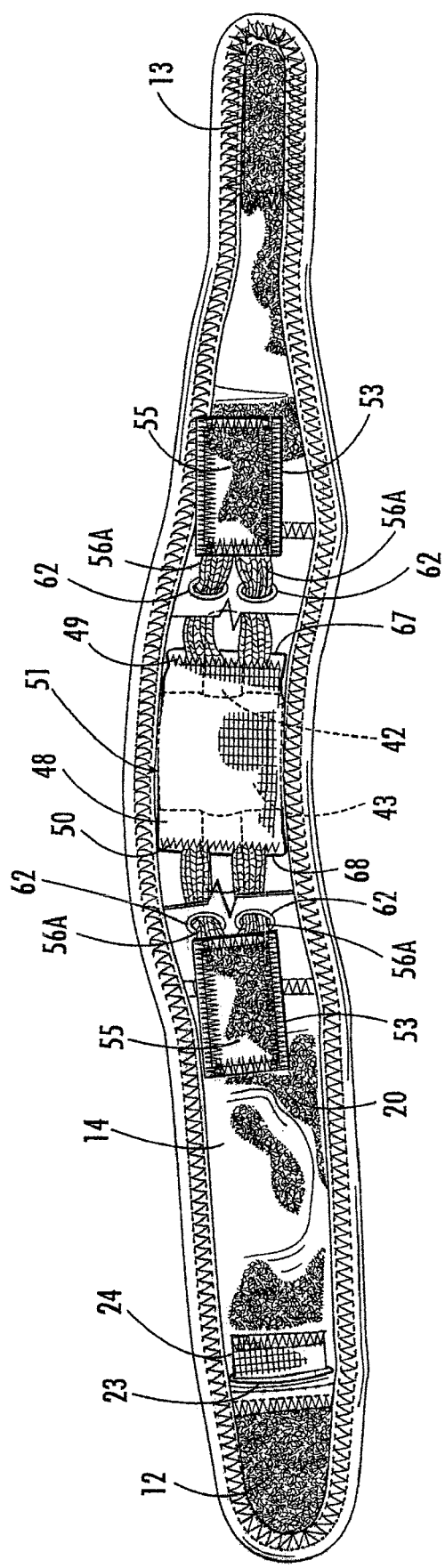
FIG. 5A is a partial cutaway view of another embodiment of the support device illustrating the manner in which the components of the secondary tensioning assembly are positioned relative to the support device.
Figure 5B:
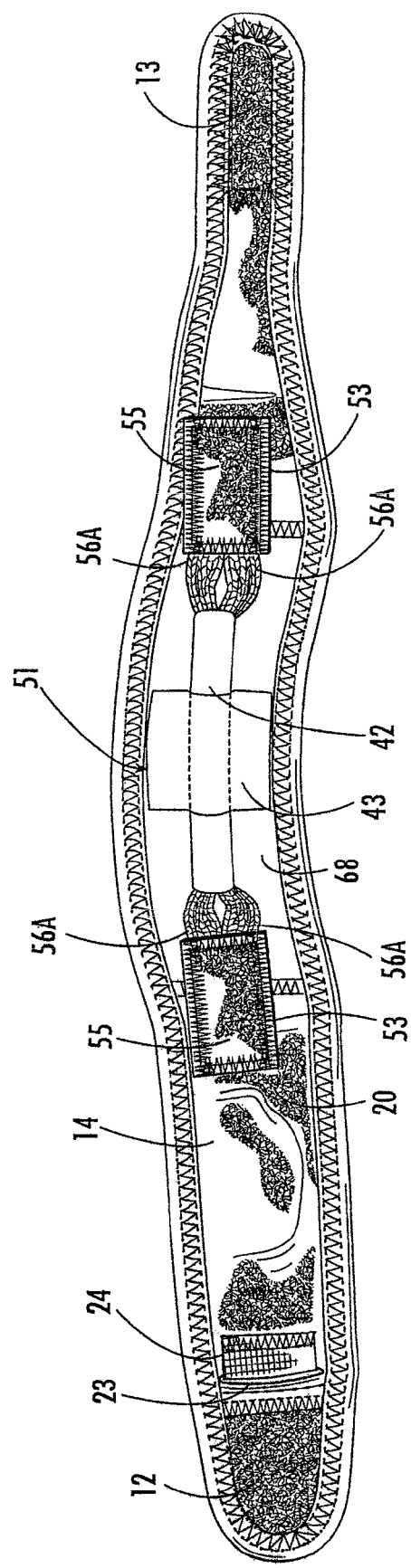
FIG. 5B is a partial cutaway view of yet another embodiment of the support device illustrating the manner in which the components of the secondary tensioning assembly are positioned relative to the support device.
Figure 6A:
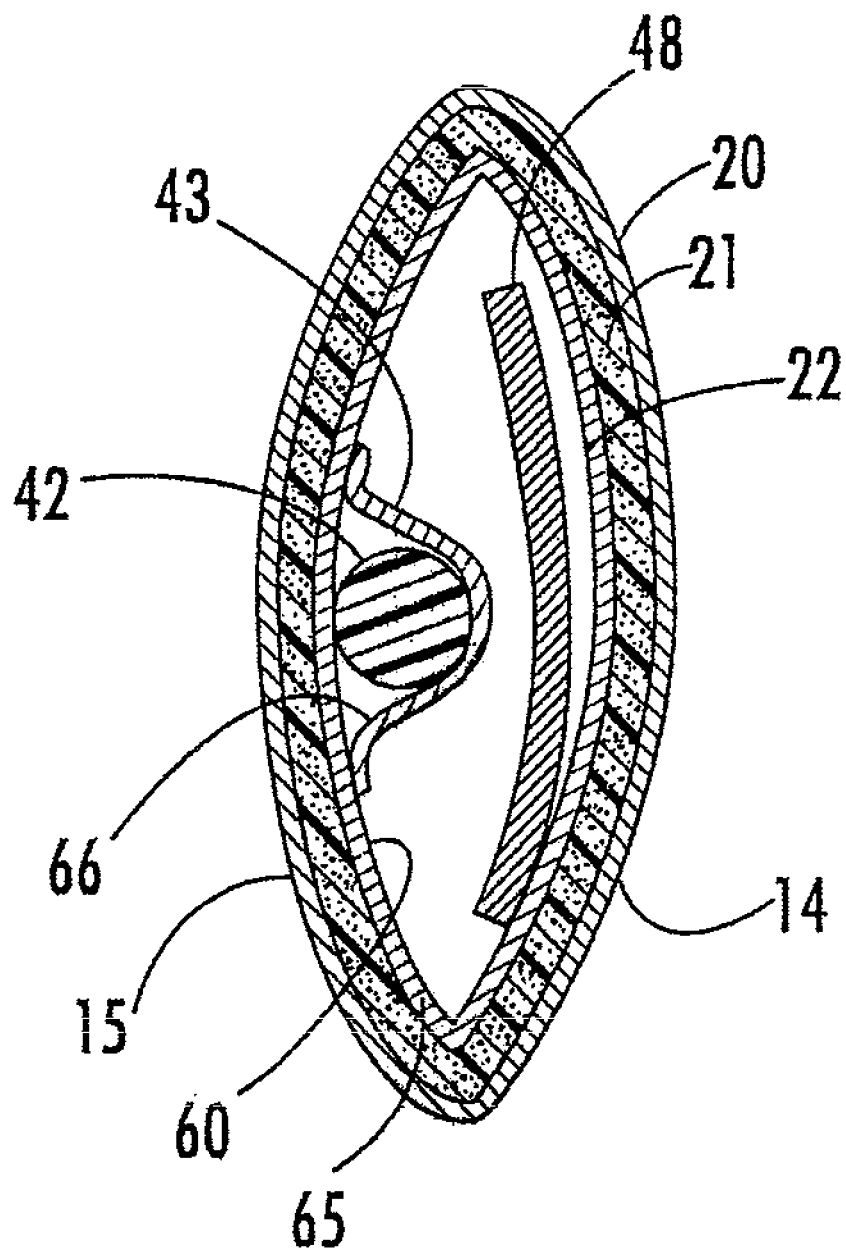

FIG. 5 shows the manner in which certain of the components of the applicator 45 are positioned within the chamber 60. The applicator 45 is assembled so that each string segment 56A extends through one of four eyelets 62 located on the front panel 14. One end of each string segment 56A is sandwiched between the elastomeric patches 47 and 48 so that two of the segments 56A are attached to each one of two opposing side edges 67 and 68, respectively. Side edges 67 and 68 are then sewn together to form the central patch 51. In an alternative embodiment depicted in FIGS. 5A and 6A that includes a central patch 51 formed from a single patch 48 (as opposed to two patches 47 and 48), one end of each string segment 56A is secured to each one of two opposing side edges of the single patch 48. In this embodiment, one end of each string segment 56A may be secured to the opposing side edges 67 and 68 of the single patch by, for example, stitching or any known manner of fixing the ends to the opposing side edges.

The other ends of each pair of string segments 56A extend to the outside of the front patch 14 and are connected to side edge 58 of one of the two fastener patches 53. As is shown in FIG. 5, the central patch 51 is positioned within chamber 60 so that it directly overlies the bar 52 and patch 43. Stated differently, the central patch 51 is positioned adjacent to the bar 52. In a preferred embodiment, the central patch 51 and bar 52 are adjacent, but not secured, to one another. As discussed above, patch 43 may form a loop 66 to hold the bar 52 against the strap 11. In an alternative embodiment, the bar 52 may be adhered to the central patch 51 with any number of known adhesives. As configured, the rod 52 is carried on the strap 11 upon assembly. It will be understood that the term "carried" as used to refer to the positional relationship of the bar 52 with respect to the strap 11 means that the bar is supported by the strap and positioned adjacent to the patch 51. This orientation is also shown in FIG. 6, and results in an increased application of force by the central patch 51 on the rod 52 when the pressure applicator 45 is being adjusted relative to the strap 11. As configured, it will be understood that the bar 52 is axially moveable independent of the strap 11 and primary tensioning device.

Another embodiment of the present invention does not include a central patch 51, or patches 47 and 48, secured to ends of the strap segments 56A. In this alternative embodiment, the bar 52 may be secured at each end to one end of each strap segment 56A with, for example, stitching, adhesive, or heat welding techniques. As configured, the patch 43 may form a loop 66 to hold the bar 52 against the strap 11. In this embodiment, the loop 66 loosely supports the bar 52 such that the bar is axially moveable about the strap 11.

In the drawings and specification, there have been disclosed typical embodiments on the invention and, although specific terms have been employed, they have been used in a generic and descriptive sense only and not for purposes of limitation, the scope of the invention being set forth in the following claims.

That which is claimed is:

1. An adjustable support device for a knee, said device comprising:
   a strap having at least one elastic portion, a first end, and a second end, said strap having interior walls that define a chamber; and
   a tensioning device supported by said strap, said tensioning device having a first end and a second end;
   an inelastic element positioned between said first and second ends of said tensioning device; and
   at least one attachment member secured to said first or second end of said tensioning device for placing said tensioning device in a secondary tensioned position;
   wherein at least a portion of said tensioning device is supported within said chamber in a way that permits said tensioning device to move axially about, yet independent of, said strap; and
   wherein said inelastic element of said tensioning device is positioned within said chamber and configured to permit said inelastic element to move axially about, yet independent of, said strap.

2. A support device according to claim 1, wherein said strap comprises:
   first and second fasteners attached to said first and second ends of said strap, respectively, said first and second fasteners cooperating with an outer surface of said strap for securing said strap around the knee and placing said strap in a primary tensioned position.

3. A support device according to claim 1, wherein said tensioning device comprises:
   an elastic element positioned between said first and second ends of said elastic element; and
   at least one attachment member secured to said first or second end of said tensioning device for placing said tensioning device in a secondary tensioned position.

4. A support device according to claim 3, wherein said elastic element of said tensioning device is positioned within said chamber such that said elastic element is axially movable independent of said strap.

5. An adjustable support device for a knee, said device comprising:
   a strap having interior walls that define a chamber and at least one elastic portion, said strap having a first end and a second end, said strap having a longitudinal axis;
   a primary tensioning device positioned on said strap for securing said strap around the knee and positioning said strap in a primary tensioned position;
   a secondary tensioning device carried by said strap, said secondary tensioning device having an elastic element and at least one attachment member, said attachment member for placing said secondary tensioning device in a secondary tensioned position; and
   a semi-rigid elongate bar secured to said strap between said first and second ends of said strap;
   wherein said secondary tensioning device includes first and second pairs of ligatures that interconnect said attachment member and said elastic element, said first and second pairs of ligatures extending through respective first and second pairs of openings defined by said strap;
   wherein said elastic element comprises one or more patches of material; and
   wherein at least a portion of said elastic element is positioned within said chamber and configured to permit said elastic element to move axially about, yet independent of, said strap and said primary tensioning device.

6. A support device according to claim 5, wherein said primary tensioning device comprises first and second fasteners attached to said first and second ends of said primary tensioning device, respectively, said first and second fasteners cooperating with an outer surface of said strap for securing said strap around the knee.

7. A support device according to claim 6, wherein:
   said first and second fasteners each comprise a patch of hooked material complementary to said outer surface of said strap; and
   said outer surface of said strap comprises looped material complementary to said first and second fasteners.

8. A support device according to claim 5, wherein said primary tensioning device further comprises:
a first opening defined by and extending through said strap adjacent to said first end, said first opening adapted for receiving said second end of said strap therethrough; and
a second opening defined by and extending through said strap adjacent to said second end, said second opening adapted for receiving said first end of said strap therethrough.

9. A support device according to claim 8, wherein each one of said first and second openings comprises an elongate slot extending perpendicularly to the longitudinal axis of said strap for permitting ease of movement of said ends of said strap therethrough.

10. A support device according to claim 5, wherein the longitudinal axis of said secondary tensioning device is aligned with the longitudinal axis of said strap.

11. A support device according to claim 5, wherein said at least one attachment member of said secondary tensioning device includes two attachment members connected to respective opposing side edges of said elastic element and releasably connected to an outer surface of said strap.

12. A support device according to claim 11, wherein:
each of said attachment members comprises a patch of hooked material complementary to said outer surface of said strap; and
said outer surface of said strap comprises looped material.

13. A support device according to claim 5, wherein said elongate bar is secured to said strap by a patch of material, said patch overlying at least a portion of said bar and secured at opposing side edges to said strap.

14. A support device according to claim 5, wherein said elongate bar is secured to said strap with adhesive.

15. A support device according to claim 5, wherein said elongate bar is positioned within said chamber between said elastic element and said interior wall adjacent to the knee.

16. A support device according to claim 5, wherein said one or more patches of material includes a single patch of material.

17. An adjustable support device for a knee, said device comprising:
a strap having interior walls that define a chamber and at least one elastic portion, said strap having a first end and a second end, said strap having a longitudinal axis;
a primary tensioning device positioned on said strap for securing said strap around the knee and positioning said strap in a primary tensioned position;
a secondary tensioning device carried by said strap, said secondary tensioning device having an elastic element and at least one attachment member, said attachment member for placing said secondary tensioning device in a secondary tensioned position; and
a semi-rigid elongate bar secured to said strap between said first and second ends of said strap;
wherein said elastic element comprises a plurality of patches of material; and
wherein at least a portion of said elastic element is positioned within said chamber and configured to permit said elastic element to move axially about, yet independent of, said strap and said primary tensioning device.

18. A support device according to claim 17, wherein said primary tensioning device comprises first and second fasteners attached to said first and second ends of said primary tensioning device, respectively, said first and second fasteners cooperating with an outer surface of said strap for securing said strap around the knee.

19. A support device according to claim 18, wherein:
said first and second fasteners each comprise a patch of hooked material complementary to said outer surface of said strap; and
said outer surface of said strap comprises looped material complementary to said first and second fasteners.

20. A support device according to claim 17, wherein said primary tensioning device further comprises:
a first opening defined by and extending through said strap adjacent to said first end, said first opening adapted for receiving said second end of said strap therethrough; and
a second opening defined by and extending through said strap adjacent to said second end, said second opening adapted for receiving said first end of said strap therethrough.

21. A support device according to claim 20, wherein each one of said first and second openings comprises an elongate slot extending perpendicularly to the longitudinal axis of said strap for permitting ease of movement of said ends of said strap therethrough.

22. A support device according to claim 17, wherein the longitudinal axis of said secondary tensioning device is aligned with the longitudinal axis of said strap.

23. A support device according to claim 17, wherein said secondary tensioning device includes first and second pairs of ligatures that interconnect said attachment member and said elastic element.

24. A support device according to claim 23, wherein said first and second pairs of ligatures extend through respective first and second pairs of openings defined by said strap.

25. A support device according to claim 17, wherein said at least one attachment member of said secondary tensioning device includes two attachment members connected to respective opposing side edges of said elastic element and releasably connected to an outer surface of said strap.

26. A support device according to claim 25, wherein:
each of said attachment members comprises a patch of hooked material complementary to said outer surface of said strap; and
said outer surface of said strap comprises looped material.

27. A support device according to claim 17, wherein said elongate bar is secured to said strap by a patch of material, said patch overlying at least a portion said bar and secured at opposing side edges to said strap.

28. A support device according to claim 17, wherein said elongate bar is secured to said strap with adhesive.

29. A support device according to claim 17, wherein said elongate bar is positioned within said chamber between said elastic element and said interior wall adjacent to the knee.

30. A support device according to claim 17, wherein said plurality of patches of material include identically-shaped patches overlaid in registration with one another and joined together along opposing side edges.

31. An adjustable support device for a knee, said device comprising:
a strap having interior walls that define a chamber and at least one elastic portion, said strap having a first end and a second end for securing said strap around the knee, said strap having a longitudinal axis;
a primary tensioning device positioned on said strap for securing said strap around the knee and positioning said strap in a primary tensioned position;
a secondary tensioning device carried by said strap, said secondary tensioning device having an inelastic element and at least one attachment member, said attachment member for placing said secondary tensioning device in a secondary tensioned position; and a semi-rigid elongate bar secured to said strap between said first and second ends of said strap;

wherein said inelastic element comprises one or more patches of inelastic material; and wherein at least a portion of said inelastic element is positioned within said chamber and configured to permit said inelastic element to move axially about, yet independent of, said strap and said primary tensioning device.

32. A support device according to claim 31, wherein said primary tensioning device comprises first and second fasteners attached to said first and second ends of said primary tensioning device, respectively, said first and second fasteners cooperating with an outer surface of said strap for securing said strap around the knee.

33. A support device according to claim 32, wherein:
said first and second fasteners each comprise a patch of hooked material complementary to said outer surface of said strap; and
said outer surface of said strap comprises looped material complementary to said first and second fasteners.

34. A support device according to claim 31, wherein said primary tensioning device further comprises:
a first opening defined by and extending through said strap adjacent to said first end, said first opening adapted for receiving said second end of said strap therethrough; and
a second opening defined by and extending through said strap adjacent to said second end, said second opening adapted for receiving said first end of said strap therethrough.

35. A support device according to claim 34, wherein each one of said first and second openings comprises an elongate slot extending perpendicularly to the longitudinal axis of said strap for permitting ease of movement of said ends of said strap therethrough.

36. A support device according to claim 31, wherein the longitudinal axis of said secondary tensioning device is aligned with the longitudinal axis of said strap.

37. A support device according to claim 31, wherein said secondary tensioning device includes first and second pairs of ligatures that interconnect said attachment member and said inelastic element.

38. A support device according to claim 37, wherein said first and second pairs of ligatures extend through respective first and second pairs of openings defined by said strap.

39. A support device according to claim 31, wherein said at least one attachment member of said secondary tensioning device includes two attachment members connected to respective opposing side edges of said inelastic element and releasably connected to an outer surface of said strap.

40. A support device according to claim 39, wherein:
each of said attachment members comprises a patch of hooked material complementary to said outer surface of said strap; and
said outer surface of said strap comprises looped material.

41. A support device according to claim 31, wherein said elongate bar is secured to said strap by a patch of material, said patch overlying at least a portion said elongate bar and secured at opposing side edges to said strap.

42. A support device according to claim 31, wherein said elongate bar is secured to said strap with adhesive.

43. A support device according to claim 31, wherein said elongate bar is positioned within said chamber between said inelastic element and said interior wall adjacent to the knee.

44. A support device according to claim 31, wherein said one or more patches of inelastic material includes a single patch of inelastic material.

45. An adjustable support device for the knee, said device comprising:
a strap having interior walls that define a chamber and at least one elastic portion, said strap having a first end and a second end, said strap having a longitudinal axis;
a primary tensioning device positioned on said strap for securing said strap around the knee and positioning said strap in a primary tensioned position; and
a secondary tensioning device carried by said strap, said secondary tensioning device having a semi-rigid elongate bar secured to said strap between said first and second ends of said strap and at least one attachment member, said attachment member for placing said secondary tensioning device in a secondary tensioned position;
wherein at least a portion of said semi-rigid elongate bar is positioned within the chamber and configured to permit said elongate bar to move axially about, yet independent of, said strap and said primary tensioning device.

46. A support device according to claim 45, wherein said primary tensioning device comprises first and second fasteners attached to said first and second ends of said primary tensioning device, respectively, said first and second fasteners cooperating with an outer surface of said strap for securing said strap around the knee.

47. A support device according to claim 46, wherein:
said first and second fasteners each comprise a patch of hooked material complementary to said outer surface of said strap; and
said outer surface of said strap comprises looped material complementary to said first and second fasteners.

48. A support device according to claim 45, wherein said primary tensioning device further comprises:
a first opening defined by and extending through said strap adjacent to said first end, said first opening adapted for receiving said second end of said strap therethrough; and
a second opening defined by and extending through said strap adjacent to said second end, said second opening adapted for receiving said first end of said strap therethrough.

49. A support device according to claim 48, wherein each one of said first and second openings comprises an elongate slot extending perpendicularly to the longitudinal axis of said strap for permitting ease of movement of said ends of said strap therethrough.

50. A support device according to claim 45, wherein the longitudinal axis of said secondary tensioning device is aligned with the longitudinal axis of said strap.

51. A support device according to claim 45, wherein:
said secondary tensioning device includes first and second pairs of ligatures that interconnect said attachment member and said elongate bar; and
wherein each end of said elongate bar is secured to at least one end of each of said first and second ligatures, respectively.

52. A support device according to claim 51, wherein said first and second pairs of ligatures extend through respective first and second pairs of openings defined by said strap.

53. A support device according to claim 45, wherein said at least one attachment member of said secondary tensioning device includes two attachment members connected to respective opposing ends of said elongate bar and releasably connected to an outer surface of said strap.

54. A support device according to claim 53, wherein:
each of said attachment members comprises a patch of hooked material complementary to said outer surface of said strap; and
said outer surface of said strap comprises looped material.

55. A support device according to claim 45, wherein said elongate bar is positioned against said strap by a patch of material, said patch overlying at least a portion said bar and secured at opposing side edges to said strap such that said bar is moveable about said strap.

56. A support device according to claim 45, wherein said elongate bar is positioned within said chamber.

57. A support device according to claim 45, wherein said elongate bar is formed from braided cord.

58. An adjustable support device for a knee, said device comprising:
a strap having interior walls that define a chamber and at least one elastic portion, said strap having a first end and a second end;
a primary tensioning device positioned on said strap for securing said strap around the knee and positioning said strap in a primary tensioned position;
a secondary tensioning device carried by said strap, said secondary tensioning device having an elastic element and at least one attachment member, said attachment member for placing said secondary tensioning device in a secondary tensioned position; and
a semi-rigid elongate bar secured to said strap between said first and second ends of said strap; said elongate bar secured to said strap by a patch of material, said patch overlying at least a portion of said bar and secured at opposing side edges to said strap;
wherein said elastic element comprises one or more patches of material; and
wherein at least a portion of said elastic element is positioned within said chamber and configured to permit said elastic element to move axially about, yet independent of, said strap and said primary tensioning device.

59. An adjustable support device for a knee, said device comprising:
a strap having interior walls that define a chamber and at least one elastic portion, said strap having a first end and a second end;
a primary tensioning device positioned on said strap for securing said strap around the knee and positioning said strap in a primary tensioned position;
a secondary tensioning device carried by said strap, said secondary tensioning device having an elastic element and at least one attachment member, said attachment member for placing said secondary tensioning device in a secondary tensioned position; and
a semi-rigid elongate bar secured to said strap between said first and second ends of said strap, said elongate bar secured to said strap with adhesive;
wherein said elastic element comprises one or more patches of material; and
wherein at least a portion of said elastic element is positioned within said chamber and configured to permit said elastic element to move axially about, yet independent of, said strap and said primary tensioning device.

60. An adjustable support device for a knee, said device comprising:
a strap having interior walls that define a chamber and at least one elastic portion, said strap having a first end and a second end;
a primary tensioning device positioned on said strap for securing said strap around the knee and positioning said strap in a primary tensioned position;
a secondary tensioning device carried by said strap, said secondary tensioning device having an elastic element and at least one attachment member, said attachment member for placing said secondary tensioning device in a secondary tensioned position; and
a semi-rigid elongate bar secured to said strap between said first and second ends of said strap, said elongate bar positioned within said chamber between said elastic element and said interior wall adjacent to the knee;
wherein said elastic element comprises one or more patches of material; and
wherein at least a portion of said elastic element is positioned within said chamber and configured to permit said elastic element to move axially about, yet independent of, said strap and said primary tensioning device.

61. An adjustable support device for a knee, said device comprising:
a strap having interior walls that define a chamber and at least one elastic portion, said strap having a first end and a second end;
a primary tensioning device positioned on said strap for securing said strap around the knee and positioning said strap in a primary tensioned position;
a secondary tensioning device carried by said strap, said secondary tensioning device having an elastic element and at least one attachment member, said attachment member for placing said secondary tensioning device in a secondary tensioned position; and
a semi-rigid elongate bar secured to said strap between said first and second ends of said strap;
wherein said elastic element comprises a single patch of material; and
wherein at least a portion of said elastic element is positioned within said chamber and configured to permit said elastic element to move axially about, yet independent of, said strap and said primary tensioning device.

* * * * *